(12) United States Patent
Delden et al.

(10) Patent No.: US 10,822,759 B2
(45) Date of Patent: Nov. 3, 2020

(54) LOAD ARRANGEMENT FOR POWERING A LOAD

(71) Applicant: KONINKLIJKE PHILIPS N.V., Eindhoven (NL)

(72) Inventors: Marc Delden, Venlo (NL); Michiel Johannes Jongerius, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/469,998

(22) PCT Filed: Dec. 14, 2017

(86) PCT No.: PCT/EP2017/082738
§ 371 (c)(1),
(2) Date: Jun. 14, 2019

(87) PCT Pub. No.: WO2018/114556
PCT Pub. Date: Jun. 28, 2018

(65) Prior Publication Data
US 2019/0352872 A1  Nov. 21, 2019

(30) Foreign Application Priority Data
Dec. 20, 2016 (EP) .................................... 16205220

(51) Int. Cl.
*E02B 17/00* (2006.01)
*H02J 50/05* (2016.01)
(Continued)

(52) U.S. Cl.
CPC ............ *E02B 17/0026* (2013.01); *A61L 2/10* (2013.01); *A61L 2/26* (2013.01); *B08B 17/02* (2013.01);
(Continued)

(58) Field of Classification Search
USPC ..................................................... 204/196.01
See application file for complete search history.

(56) References Cited

U.S. PATENT DOCUMENTS 5,182,007 A   1/1993   Takagi et al.
5,322,569 A   6/1994   Titus et al.
(Continued)

FOREIGN PATENT DOCUMENTS

EP   468739 A1   1/1992
GB   842297 A    7/1960
(Continued)

OTHER PUBLICATIONS

International Search Report and Written Opinion, International Application No. PCT/EP2017/082738, dated Jan. 29, 2018.
(Continued)

*Primary Examiner* — Kiet T Nguyen

(57) ABSTRACT

A load arrangement is provided for powering a load on a surface (30) of a marine structure (50) exposed to a liquid (10). The load arrangement has a carrier (100) and a conductor arrangement (110) arranged on the surface of the marine structure and coupled to one pole of a power source (1). The other pole is coupled to the liquid. The carrier has a back surface (102) to cover part of the conductor arrangement and the surface (30) of the marine structure. A load (20) in the carrier receives supply current from the power source via a front electrode (130) arranged for coupling to the liquid, and a back electrode (120) at the back surface arranged for coupling to the conductor arrangement. The load may be an UV-C LED for emitting anti-fouling light.

14 Claims, 3 Drawing Sheets

(51) Int. Cl.
*A61L 2/10* (2006.01)
*A61L 2/26* (2006.01)
*B08B 17/02* (2006.01)
*B63B 35/44* (2006.01)
*B63B 59/08* (2006.01)
*C23F 13/02* (2006.01)
*B63B 59/04* (2006.01)
*C23F 13/04* (2006.01)
*C23F 13/16* (2006.01)
*C23F 13/20* (2006.01)
*G01N 17/02* (2006.01)

(52) U.S. Cl.
CPC .............. *B63B 35/44* (2013.01); *B63B 59/04* (2013.01); *B63B 59/08* (2013.01); *C23F 13/02* (2013.01); *C23F 13/04* (2013.01); *C23F 13/16* (2013.01); *C23F 13/20* (2013.01); *G01N 17/02* (2013.01); *H02J 50/05* (2016.02); *A61L 2202/11* (2013.01); *B63B 2035/4433* (2013.01); *C23F 2213/31* (2013.01)

(56) References Cited

U.S. PATENT DOCUMENTS

| | | |
|---|---|---|
| 7,064,459 B1 | 6/2006 | Staerzl |
| 7,950,452 B2 | 5/2011 | Lutz |
| 2006/0065551 A1 | 3/2006 | Howard, Jr. et al. |
| 2010/0199906 A1 | 8/2010 | Stieglitz |
| 2019/0008009 A1* | 1/2019 | Van Delden ............ H01L 33/36 |
| 2019/0014631 A1* | 1/2019 | Van Delden ........... H05B 45/37 |
| 2020/0047227 A1* | 2/2020 | Hietbrink ............. G02B 6/0031 |

FOREIGN PATENT DOCUMENTS

| | | |
|---|---|---|
| WO | 2007107722 A1 | 9/2007 |
| WO | 2014188347 A1 | 11/2014 |
| WO | 2016193055 A1 | 12/2016 |
| WO | 2017109063 A1 | 6/2017 |

OTHER PUBLICATIONS

B.A. Salters, C.G. Visser, E.A.W. Janssen, P.A.H. Snoeijen, and R.B. Hietbrink, Shipshape-Runwell, PR-TN 2016/00140, 2013.

Bart Salters and Roelant Hietbrink, Progress in Philips RunWell UV-based antifouling technology, ICMCF 2016 presentation 38B.

Bart Salters, Richard Piola, Roelant Hietbrink, Clare Grandison, and Marc Ciacic, Prevention of biofouling using UV-light emission from low voltage miniature LEDs, Pacific 2015.

Richard Piola, Clare Grandison, Mark Ciacic, Bart Salters, and Roelant Hietbrink, Low voltage UV LEDs for marine biofoufing control: Laboratory and field testing, ICMCF 2016 presentation 48B.

* cited by examiner

LOAD ARRANGEMENT FOR POWERING A LOAD

CROSS-REFERENCE TO PRIOR APPLICATIONS

This application is the U.S. National Phase application under 35 U.S.C. § 371 of International Application No. PCT/EP2017/082738, filed on Dec. 14, 2017, which claims the benefit of EP Patent Application No. EP 16205220.3, filed on Dec. 20, 2016. These applications are hereby incorporated by reference herein.

FIELD OF THE INVENTION

The invention relates to a load arrangement for powering a load on a surface of a marine structure exposed to a liquid, such as seawater. The liquid constitutes an electrically conductive medium. The load is embedded in a carrier and is coupled between a first power node and a second power node for receiving supply current from a power source.

BACKGROUND OF THE INVENTION

Biofouling of surfaces which are exposed to water, during at least a part of their lifetime, is a well-known phenomenon, which causes substantial problems in many fields. For example, in the field of shipping, biofouling on the hull of ships is known to cause a severe increase in drag of the ships, and thus increased fuel consumption of the ships. In this respect, it is estimated that an increase of up to 40% in fuel consumption can be attributed to biofouling.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro fouling which includes biofilm formation and bacterial adhesion, and macro fouling which includes the attachment of larger organisms. Due to the distinct chemistry and biology that determine what prevents them from settling, organisms are also classified as being hard or soft. Hard fouling organisms include calcareous organisms such as barnacles, encrusting bryozoans, mollusks, polychaetes and other tube worms, and zebra mussels. Soft fouling organisms include non-calcareous organisms such as seaweed, hydroids, algae and biofilm "slime". Together, these organisms form a fouling community.

As mentioned in the foregoing, biofouling creates substantial problems. Biofouling can cause machinery to stop working and water inlets to get clogged, to mention only two other negative consequences than the above-mentioned increase of drag of ships. Hence, the topic of anti-biofouling, i.e. the process of removing or preventing biofouling, is well-known.

WO 2014/188347 A1 describes a method of anti-fouling of a surface while said surface is at least partially submersed in a liquid environment, in particular an aqueous or oily environment. The method involves providing an anti-fouling light from light sources embedded in an optical medium on the exposed surface, the optical medium having a substantially planar emission surface. The anti-fouling light is emitted from the emission surface of the optical medium, in a direction away from the exposed surface, and the anti-fouling light may be ultraviolet light. The light sources need to be electrically powered and so constitute an example of loads to be powered on a surface of a marine structure. WO 2014/188347 A1 describes to power such loads via wires embedded in said optical medium.

SUMMARY OF THE INVENTION

It follows from the foregoing that WO 2014/188347 A1 addresses the subject of providing anti-fouling light on a surface of a marine structure. The electrical loads are embedded in a carrier and powered via wires embedded in the carrier. For connecting respective carriers to a power source, galvanic connections have to be made, e.g. using power lines and power connectors, which is expensive and unreliable. So, there is a need to provide power to such light sources and other loads in a more convenient and reliable way.

The invention has as an object to provide a load arrangement for powering loads on an exposed surface.

According to the invention, a load arrangement is provided for powering a load on a surface of a marine structure exposed to a liquid, the liquid constituting an electrically conductive medium, the load arrangement comprising:

a conductor arrangement to be arranged on the surface of the marine structure and structured for coupling to one pole of a power source, the other pole of the power source being coupled to the electrically conductive medium;

a carrier having a front surface to be in contact with the liquid and a back surface to cover part of the conductor arrangement and the surface of the marine structure, and the carrier comprising a load arranged in the carrier and coupled between a first power node and a second power node for receiving supply current from the power source, a front electrode at the front surface, connected to the first power node and arranged for coupling to the electrically conductive medium, and a back electrode at the back surface, connected to the second power node and arranged for coupling to the conductor arrangement.

According to the invention, a marine structure is provided having a surface to be exposed to a liquid, the liquid constituting an electrically conductive medium, the marine structure comprising at least one load arrangement as defined above, wherein the conductor arrangement is arranged on the surface of the marine structure;

the carrier is arranged at the surface of the marine structure having the back surface covering part of the conductor arrangement and the surface of the marine structure;

the back electrode is coupled to the conductor arrangement, and the marine structure comprises the power source having one pole connected to the conductor arrangement and the other pole coupled to the electrically conductive medium for transferring the supply current from the power source to the load.

According to the invention, a method is provided for installing a load arrangement as defined above, the method comprising attaching the conductor arrangement to a surface of a marine structure to be exposed to the liquid;

arranging the back surface of the carrier covering part of the conductor arrangement and the surface of the marine structure, while coupling the back electrode to the conductor arrangement; and providing the power source coupled between the electrically conductive medium and the conductor arrangement for transferring the supply current from the power source to the load.

The above features have the following effect. The carrier is a mechanical element that physically carries the one or more loads, e.g. light sources embedded in or located on the carrier. The carrier has a front surface in contact with the liquid and a back surface to cover at least part of the conductor arrangement and the surface of the marine structure. In the carrier one or more loads are embedded. Each load is coupled between a first power node and a second power node for receiving supply current from the power source. The carrier has one or more front electrodes located at the front surface, and back electrodes at the back surface. The power source has two poles, one pole is to be connected to the conductor arrangement and the other pole of the power source is to be coupled to the electrically conductive medium. A respective front electrode is connected to the first power node and is arranged for coupling to the electrically conductive medium. In use, the supply current is transferred from said other pole of the power source to the front electrode via the electrically conductive medium, e.g. seawater. A respective back electrode is connected to the second power node and arranged for coupling to the conductor arrangement.

In use, the conductor arrangement is arranged on the surface of the marine structure and has a structure that is coupled to one pole of a power source, for example a direct galvanic connection via a power line. The other pole of the power source is coupled to the electrically conductive medium, e.g. via one or more conductive transmitters extending into the liquid, or via bare metal parts of the marine structure. On the surface of the marine structure to be exposed to the liquid, first the conductor arrangement is applied and subsequently, on top of the conductor arrangement, the carrier is applied to the surface of the marine structure. Advantageously, at least the part of the conductor arrangement that is structured for coupling to the one or more back electrodes is between the carrier and the surface of the marine structure. So, connections between the back electrodes and the conductor arrangement may be covered by the carrier, e.g. shaped as tiles or a sheet, and are so protected from the liquid.

Effectively, the carrier having back electrodes at the back surface arranged for coupling to the conductor arrangement is positioned on top of the conductor arrangement having a structure for coupling to the one or more back electrodes. Hence, electric coupling is achieved from the back electrodes to the conductor arrangement so as to transfer the supply current. The supply current is transferred from one pole of the power source to the front electrodes via the conductive medium. Sequentially, the supply current is transferred from said one pole of the power source via the electrically conductive medium, the first electrode, the first power node, the light source, the second power node, the second electrode and the conductor arrangement back to the other pole of the power source. Advantageously, the conductor arrangement only provides a single conductive path to one pole of the power source, while crossings of two conductors to the respective two poles of the power source are avoided by using the conductive medium, i.e. said liquid, as the other power transfer path.

In an embodiment of the load arrangement, the front electrode comprises a conductive part at the front surface galvanically in contact with the liquid for transfer of the supply current between the first power node and the electrically conductive medium. Effectively, the front electrode is in conductive contact with the electrically conductive medium, and may conduct both AC and DC current.

In an embodiment of the load arrangement, the front electrode comprises a front electrically conductive layer embedded in the carrier near the front surface, the embedded layer being arranged to form, in combination with a dielectric layer and the liquid, a front capacitor for capacitive transfer of the supply current between the first power node and the electrically conductive medium. Effectively, the capacitance is formed by the front electrically conductive layer and the liquid constituting an electrically conductive medium, via a dielectric layer formed by the carrier material. Advantageously, such capacitance may conduct AC current of an appropriate frequency, while also limiting the amount of current in the event of a short-circuit or malfunction of the load.

In an embodiment of the load arrangement, the conductor arrangement comprises metallic conductors to be arranged in a pattern distributed across the surface of the marine structure for coupling to a multitude of back electrodes of one or more carriers. One or more back electrodes are arranged for coupling to the metallic conductors. The metallic conductors may, for example, be metal strips or bars that can be easily interconnected to constitute said pattern distributed across the surface. In practice, such pattern may be applied to the surface of the marine structure before applying the carrier. The metallic conductors may be structured for coupling to a multitude of back electrodes in one or more carriers. For example, the metallic conductors may have parts that are not isolated to be located corresponding to positions of the back electrodes in the respective carrier or carriers.

Optionally, in the above load arrangement, the metallic conductors and at least one of the back electrodes are arranged for galvanic coupling. The galvanic coupling, i.e. an electrically conductive connection, connects the back electrode to the power source and advantageously enables transfer of any type of AC and DC current that is appropriate for the load. The back electrode may be arranged for galvanic coupling to the conductor arrangement for enabling the power source to yield impressed current cathodic protection of the marine structure via a DC offset added to the supply voltage. Effectively, as both electrodes conduct DC current via the load, a DC offset may be applied with respect to the marine structure. i.e. to have a DC voltage with respect to metallic conductive parts of that marine structure.

Optionally, a marine structure has a load arrangement, wherein the front electrode comprises a conductive part at the front surface galvanically in contact with the liquid for transfer of the supply current between the first power node and the electrically conductive medium and the back electrode is arranged for galvanic coupling to the conductor arrangement for galvanically connecting the back electrode to the power source. The marine structure also has a power source arranged to yield impressed current cathodic protection (ICCP) of the marine structure by adding, to the supply voltage, a DC offset with respect to the marine structure. Advantageously, ICCP is provided in combination with other loads operating on the surface to be protected, such as UV light sources for anti-fouling. Moreover, when loads and corresponding front electrodes are distributed across the surface, a distributed electrode is formed to yield said ICCP.

Optionally, in the above load arrangement, at least one of the back electrodes comprises a back electrically conductive layer embedded in the carrier near the back surface to form, in combination with a back dielectric layer and an opposite area of the metallic conductors, a back capacitor for capacitive transfer of the supply current between the second power node and the metallic conductors. Effectively the capacitance is formed by the back electrically conductive layer and the metallic conductor area, via a dielectric layer formed by the carrier material. Advantageously, such capacitance may conduct AC current of an appropriate frequency, while also limiting the amount of current in the event of a short-circuit or malfunction of one of the loads without affecting the operation of the remainder of the functional loads.

In an embodiment of the load arrangement, the conductor arrangement comprises a multi-lead cable configured to connect the leads to one pole of the power source and for separating and distributing the leads across the surface of the marine structure for coupling to a multitude of back electrodes. The multitude of leads starts at the power source connected to said one pole, and is subsequently used to be separated and distributed across the surface. Each lead may be connected to one or more back electrodes, e.g. via cooperating connector elements. Advantageously, making interconnections within the pattern of conductors is avoided, as said respective leads directly connect multiple, respective areas having respective carriers to the pole of the power source.

In an embodiment of the load arrangement, the conductor arrangement comprises a wire-mesh structured for coupling to a multitude of back electrodes in a multitude of carriers and distributing the wire-mesh across the surface of the marine structure. Advantageously, a wire-mesh is a two-dimensional structure that can be easily distributed across a surface to be covered, while spaces in between the wires of the wire-mesh remain open for directly attaching the carrier or carriers to the surface of the marine structure.

In an embodiment of the load arrangement, the carrier is shaped as a tile and comprises multiple of said loads having interconnected second power nodes, and the load arrangement comprises connector elements corresponding to edges of the tile for interconnecting neighboring tiles. Advantageously, a structure having a grid of conductors and connectors corresponding to edges of tiles is a two-dimensional structure that can be easily distributed across a surface to be covered, while spaces in between the conductors of the grid remain open for directly attaching the tiles to the surface of the marine structure.

In an embodiment of the load arrangement, the carrier comprises an inductor connected in series with the load for constituting, in combination with at least one of the back and front capacitors, a circuit resonant at a resonance frequency for cooperating with the power source generating an AC supply voltage at the resonance frequency. Effectively, by forming a resonant circuit, the impedance of the circuit as present between the conductors of the conductor arrangement and the liquid is lowered. Advantageously, a lower AC voltage at the power source is sufficient for delivering a required supply current for the load. In an embodiment of the load arrangement, the carrier comprises a capacitor connected in series with the load. Advantageously, such capacitance may conduct AC current of an appropriate frequency, while also limiting the amount of current in the event of a short-circuit or malfunction of the load.

In an embodiment of the load arrangement, the carrier may comprise an optical medium and the load may comprise an UV light source for emitting anti-fouling light for anti-fouling of the carrier and/or a surface of the marine structure in contact with the liquid, the liquid being a fouling liquid containing biofouling organisms. In a practical embodiment of the load arrangement, the carrier may be an optical medium in the form of a slab or sheet, wherein the front surface is an emission surface for emitting the anti-fouling light, while the both surfaces of the optical medium are substantially planar and extend substantially parallel to each other. In that embodiment, the optical medium is very well suitable to be applied as a cover to the exposed surface. The load may be a light source to be adapted to emit ultraviolet light. A general advantage of using ultraviolet light for anti-biofouling is that the microorganisms are prevented from adhering and rooting on the surface to be kept clean. The light source may be embedded in the optical medium, or may be arranged outside of the optical medium, at a position adjacent the optical medium.

When the light source is adapted to emit ultraviolet light, it is advantageous for the optical medium to comprise an ultraviolet transparent material such as ultraviolet transparent silicone. In a general sense, the fact that the optical medium comprises material that is configured to allow at least part of the anti-fouling light to distribute through the optical medium may be understood such as to imply that the optical medium comprises material that is substantially transparent to the anti-fouling light.

It is a practical possibility for the load arrangement according to the invention to comprise a single optical medium and a plurality of light sources. The medium may also comprise one or more mirrors to reflect light to the emission surface. In such a case, the optical medium of the load arrangement can be of any suitable shape and size, wherein light sources such as LEDs are distributed throughout the optical medium, and wherein the light emitted by each of the light sources is distributed across the emission surface of the optical medium to an optimized extent. The light sources can be arranged in a series of parallel connections in a grid to the respective front and back electrodes.

The invention is applicable in various contexts. For example, the load arrangement according to the invention may be applied in the context of a marine vessel. Optionally, a marine structure to be exposed to a liquid has a surface comprising the above load arrangement, wherein the load arrangement is attached to said exposed surface, for example the loads comprising UV light sources for anti-fouling of the exposed surface when immersed in a fouling liquid containing biofouling organisms. Also, in a method for installing the above load arrangement, the method may comprise the step of attaching the load arrangement to an exposed surface of a marine structure. Also, use of the above load arrangement is foreseen, while the load arrangement is installed to an exposed surface of a marine structure, e.g. for anti-fouling of the exposed surface when immersed in a fouling liquid containing biofouling organisms. In such contexts, the load arrangement is arranged so as to have a function in keeping, for example, a vessel's hull clean from biofouling, which does not alter the fact that numerous other application possibilities exist in that context as well.

The above-described and other aspects of the invention will be apparent from and elucidated with reference to the following detailed description of embodiments.

BRIEF DESCRIPTION OF THE DRAWINGS

These and other aspects of the invention will be apparent from and elucidated further with reference to the embodiments described by way of example in the following description and with reference to the accompanying drawings, in which.

The figures are purely diagrammatic and not drawn to scale. In the Figures, elements which correspond to elements already described may have the same reference numerals.

DETAILED DESCRIPTION OF EMBODIMENTS

Figure 1:
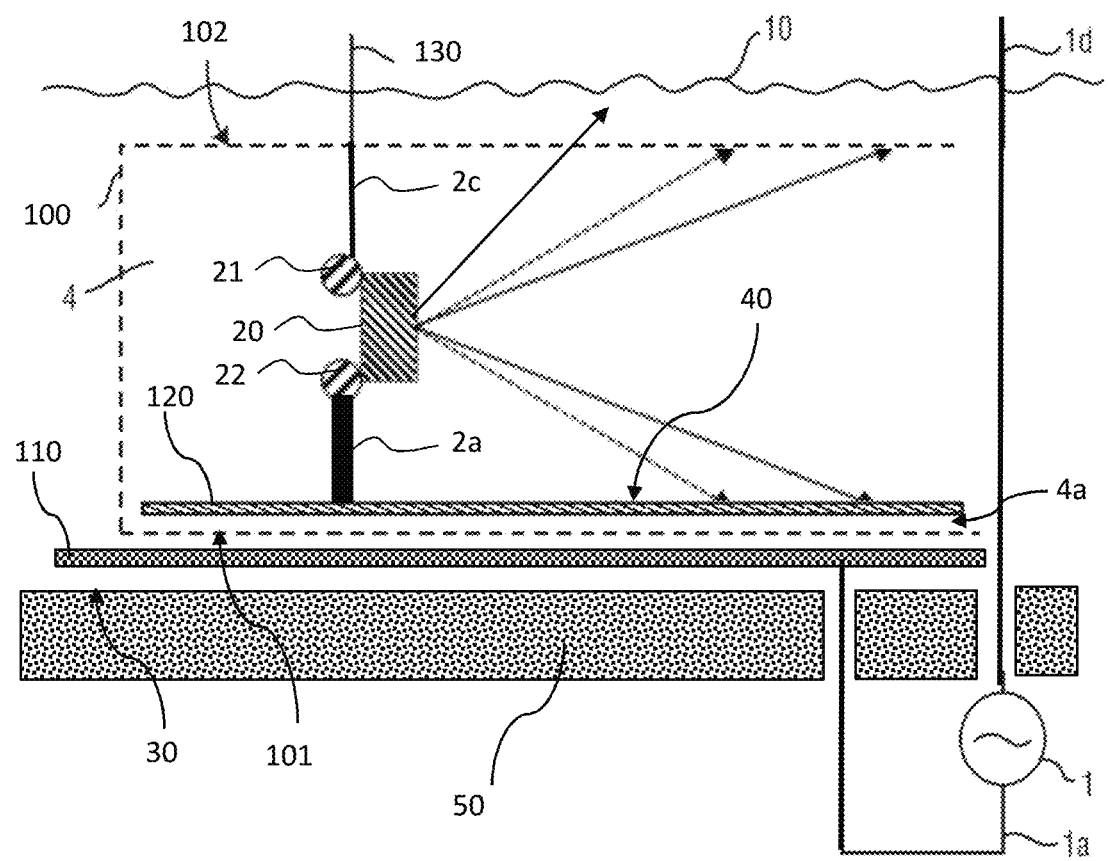
FIG. 1 shows an example of a load arrangement.

In the following, the present invention will be explained with reference to an application scenario, in which the load arrangement is used for powering of UV light sources (in particular LEDs), that may be mounted to the exposed surface of a ship hull to counter bio-fouling. However, any other load on the surface of a marine structure may be powered according to the invention, e.g. a sonar unit or other sensors. Before the details of various embodiments of disclosed subject matter will be explained, the general idea and known approaches to counter bio-fouling in such an application scenario will be discussed.

A light source in the load arrangement may be chosen for anti-fouling to specifically emit ultraviolet light of the C type, which is also known as UVC light, and even more specifically, light with a wavelength roughly between 220 nm and 300 nm. In practice the peak efficiency is achieved around 265 nm, with a fall-off towards higher and lower wavelengths. At 220 nm and at 300 nm, is has dropped to ~10% efficiency.

It has been found that most fouling organisms are killed, rendered inactive, or rendered unable to reproduce by exposing them to a certain dose of the ultraviolet light. A typical intensity which appears to be suitable for realizing anti-biofouling is 10 mW per square meter. The light may be applied continuously or at a suitable frequency, whatever is appropriate in a given situation, especially at a given light intensity. An LED is one type of UVC lamp which may be applied as the light source of the load arrangement. It is a fact that LEDs can generally be included in relatively small packages and consume less power than other types of light sources. Also, LEDs can very well be embedded in a slab of material. Furthermore, LEDs can be manufactured to emit (ultraviolet) light of various desired wavelengths, and their operating parameters, most notably the output power, can be controlled to a high degree. The LED may be a so-called side-emitting LED, and may be arranged in the optical medium so as to emit the anti-fouling light in directions along the plane of the sheet.

Anti-fouling light may be distributed through an optical medium comprising a silicone material and/or UV grade (fused) silica, and emitting the anti-fouling light from the optical medium and from the surface of a marine structure. UV-C irradiation prevents the (initial) settlement of micro- and macro organisms, for instance on a ship hull. The problem with bio-films is that as their thickness increases over time due to growth of the organisms its surface roughens. Hence, the drag increases, requiring the engine to consume more fuel to maintain the ship's cruising speed, and thus the operational costs increase. Another impact of bio-fouling can be a reduction in the cooling capacity of a pipe radiator or a flow capacity reduction of salt water intake filters and pipes. Therefore, service and maintenance costs increase.

A potential solution to counter bio-fouling of the ship hull can be the coverage of the exterior hull with slabs of for example UV-C transparent materials having embedded UV-C LED(s). These slabs, or generally any load arrangement (i.e. elements or arrangements consuming electrical energy for generating light), are located below the waterline. This is because the submerged surfaces are predominantly sensitive to bio-fouling and, hence, responsible for the increase in drag. Hence, electrical power needs to be delivered under the water-line towards the loads.

The combination of electricity, water and the rough and tough environment of the off-shore industry poses a real challenge. This is because (sea) water is a good electric conductor and, hence, short circuits may easily arise. Furthermore, water decomposes under the influence of an electrical current. In the case of sea water, it decomposes under DC current in chlorine and hydrogen gas. Under AC current, both gasses are formed alternatingly at each electrode. An additional problem with the gasses formed is that chlorine can enhance the already natural occurring corrosion of the steel ship hull and accelerates the degradation of other materials including the UV-C LEDs if not hermetically sealed. The hydrogen gas on the other hand can cause iron embrittlement, eventually leading to severe crack formation within the iron bulk.

To counter natural corrosion of the steel hull most ships are coated or painted and in addition often equipped with passive or active cathodic protecting systems such that the ship hull remains protected against natural corrosion when the protective coat or paint fails locally. Passive systems use sacrificial Zinc, Aluminum or Iron anodes that dissolve electro-chemically over time, whereas active systems impress a DC current in using anodes made of MMO-Ti (mix metal oxides) coated Titanium or Pt/Ti (Platinum coated Titanium). For active systems impressing a DC current (impressed current cathodic protection, ICCP) into the sea water, careful monitoring is required. Too large current may cause iron embrittlement due to excessive hydrogen formation, whereas too large small currents may cause under protection allowing the iron hull to still dissolve slowly. Obviously, anti-fouling solutions should not render the cathodic protection system to fail.

Various loads, such as UV LEDs of a biofouling prevention system, require electrical power. UV LEDs are two leaded, polarity sensitive light-sources, which require a DC current to operate. In conventional approaches, wired conductors can be used to provide supply current by means of galvanic contacts. However, traditional fully-wired approaches require complex wiring and connector schemes in order to connect the power source with the loads. A single-wire approach is now described which uses the sea water as a common conductive medium to a power transmitter immersed in the sea water, e.g. (parts of) the metal ship's hull connected to one pole of a power source. Said single wire is provided by a conductor arrangement as described below, which is isolated from said conductive medium.

FIG. 1 shows an example of a load arrangement. In the example, the load is a light source 20 for anti-fouling of a surface 30 of a marine structure 50 exposed to a liquid 10 constituting an electrically conductive medium, for example a fouling liquid like sea water containing biofouling organisms. The load arrangement comprises a carrier 100 as indicated by dashed lines and a conductor arrangement 110 shown to be positioned between the carrier 100 and the surface 30 of the marine structure. The carrier has a front surface 102 facing the fouling liquid and a back surface 101 covering, at least partly, the surface 30 and the conductor arrangement. A load 20 is embedded in the carrier and is coupled between a first power node 21 and a second power node 22 for receiving supply current from a power source 1.

A front electrode 130 is located at the front surface 101, and is connected to the first power node 21 via a conductor 2c. The front electrode 130 is arranged for coupling to the electrically conductive medium 10. In the example, the front electrode extends into the liquid to make galvanic contact. A back electrode 120 is located at the back surface 102, and is connected to the second power node 22 via a conductor 2a. The back electrode is arranged for coupling to the conductor arrangement, as elucidated below. The conductor arrangement 110 is connected to on pole of the power source 1 via a supply line 1a. For example, the conductor arrangement may have metal strips, a grating or a mesh or another form of isolated conductors distributed across the surface of the marine structure and connected to the power supply. The other pole of the power source is coupled to a transmitter 1d. In the example, the transmitter 1d extends into the liquid to make galvanic contact with the liquid, for transferring supply current via the electrically conductive medium to the front electrode 130. Alternatively, the power transmitter may be formed by the marine structure itself having conductive parts immersed in the liquid, e.g. (parts of) the metal ship's hull connected to one pole of a power source. Alternative connections of the front electrode to the power source are may also be considered, e.g. coupling to the liquid via a capacitor as discussed below.

The carrier may comprise an optical medium 4 and be shaped in sheet form. The front surface of the optical medium constitutes an emission surface, and may be substantially planar to the back surface of the carrier, the sea surfaces extending substantially parallel to each other. The Figure diagrammatically shows a sectional view of a portion of an optical medium, a LED constituting a load embedded in the optical medium, and a mirror 40 that may be present near the back surface of the optical medium. Possible paths of light beams are diagrammatically indicated by means of arrows. The light source may be adapted to emit ultraviolet light, for example an UV-C LED as elucidated in the section above. The optical medium allows at least part of the light to distribute through the optical medium, as shows by the arrows emanating from the light source, propagating and reflecting internally in the layer of the optical medium. In the examples one light source is shown and explained. In practice, the load arrangement may comprise a single optical medium and a plurality of light sources, and a corresponding, associated plurality of mirrors. Each of the mirrors may be electrically coupled to one or more of the light sources.

The mirror may constitute the back electrode, being electrically conductive and electrically coupled to the light source at the second power node 22 by lead 2a. For example, the mirror is a thin metallic layer of a reflective, conductive metal. At least part of the mirror may be a scattering layer. In the embodiment as shown in FIG. 1 the back electrode 120 is arranged to form a capacitor in combination with a dielectric layer 4a and an area of the conductor arrangement, for example a metallic part positioned opposite the back electrode. The capacitor enables capacitive transfer of electrical power between the front electrode and the conductor arrangement, the power source 1 being an AC power source operating at a frequency that enables sufficient supply power via the capacitor. Alternative connections of the back electrode to the conductor arrangement may be considered, e.g. a galvanic connection as discussed below.

In practice the load arrangement may have multiple loads, e.g. a pattern of multiple light sources and associated mirrors to cover an extended area while substantially provided homogeneous light emission from the emission surface. In such arrangement, the galvanic or capacitive connections may be shared by multiple loads.

Figure 2:
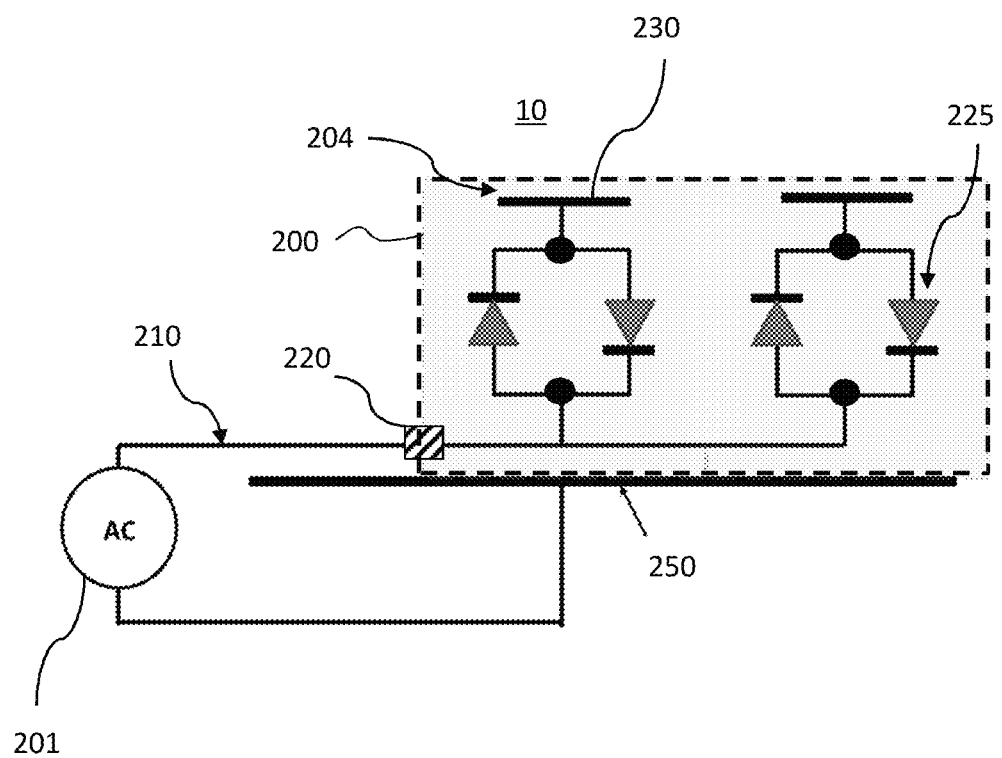
FIG. 2 shows a second example of a load arrangement having a capacitive front electrode.

FIG. 2 shows a second example of a load arrangement having a capacitive front electrode. In the example, the load is a set 225 of UV-C LEDs for emitting anti-fouling light coupled between first and second power nodes shown as black dots. The load arrangement comprises a carrier 200 as indicated by dashed lines and a conductor arrangement 210 shown as a conductor coupled to a back electrode 220. In a practical embodiment, the conductor arrangement has metallic conductors arranged in a pattern distributed across the surface of the marine structure for coupling to a multitude of back electrodes of one or more carriers. The back electrodes are arranged for coupling to the metallic conductors. In the example, the metallic conductors and at least one of the back electrodes are arranged for galvanic coupling. The load arrangement may be similar to the example shown in FIG. 1. A front electrode 230 has a front electrically conductive layer embedded in the carrier near the front surface of the carrier. The embedded layer forms, in combination with a dielectric layer 204 and the liquid 10, a front capacitor for capacitive transfer of the supply current between the first power node and the electrically conductive medium.

In FIG. 2, an AC power source 201 (e.g. in the 100-440 kHz region or at 7.56 or 13.56 MHz) is connected to the LED's (here shown in anti-parallel pairs, so that both semi-phases are used for UV generation) through the conductor arrangement 210 constituting a single-wired connection. The second electrical power connection is made through said capacitors coupled to the sea water. The sea water provides a common electrically conductive path to unprotected metal areas of the marine structure 250, e.g. parts of a ship's hull, a propeller or a rudder or other in the sea water submerged metallic regions of the marine structure (e.g. bow thruster tunnel). Effectively, it does not matter how the current flows back from the transmitters towards the hull, scratch, anchor, propeller and other shorts.

Next to avoiding the occurrence of undesired DC components in the circuit, potentially leading to (electro-chemical) corrosion phenomena, the capacitive coupled transmitters can also serve as current limiters for the LED's. For driving a single pair of anti-parallel UV-LED's at about 100 kHz, a capacity value for the transmitter is required that corresponds with a transmitter area that may be larger than the area to be kept clean by the UVC from these LED's. Hence, alternatively to the planar capacitive transmitter, more compact discrete (ceramic) capacitors can be used equipped with sea water borne Pt/Ti wires to provide the electrical connection to the sea water. Another option is to apply a higher drive frequency (e.g. >2 MHz).

Optionally, the carrier may be shaped as a tile and comprise multiple of said loads. The loads may have interconnected second power nodes. In the case of multiple carriers, e.g. a tiling of an anti-fouling layer, the conductor arrangement may have further wires to be connected from tile to tile. For this purpose, below the layer of tiles, the conductor arrangement may have a separate layer of a wire mesh, fishbone or similar pattern that is locally capacitive, resistive or galvanic coupled to the leads forming back electrodes of the anti-fouling tiles on top of this layer.

Alternatively, a grid of local interconnection patches in a layer below the tiles can be used to connect with complementary parts in the tiles. For example, the load arrangement may have connector elements corresponding to edges of the tile for interconnecting neighboring tiles. The carriers may be provided with connector elements on the edges, while the conductor arrangement has complementary connector elements on positions corresponding to the edges. The coupling may be made capacitive or galvanic. A capacitive coupling, as illustrated in FIG. 1, may be more feasible as similar capacitors in series in the supply chain will have a similar potential drop, which can be taken into account when selecting the AC power source.

Figure 3:
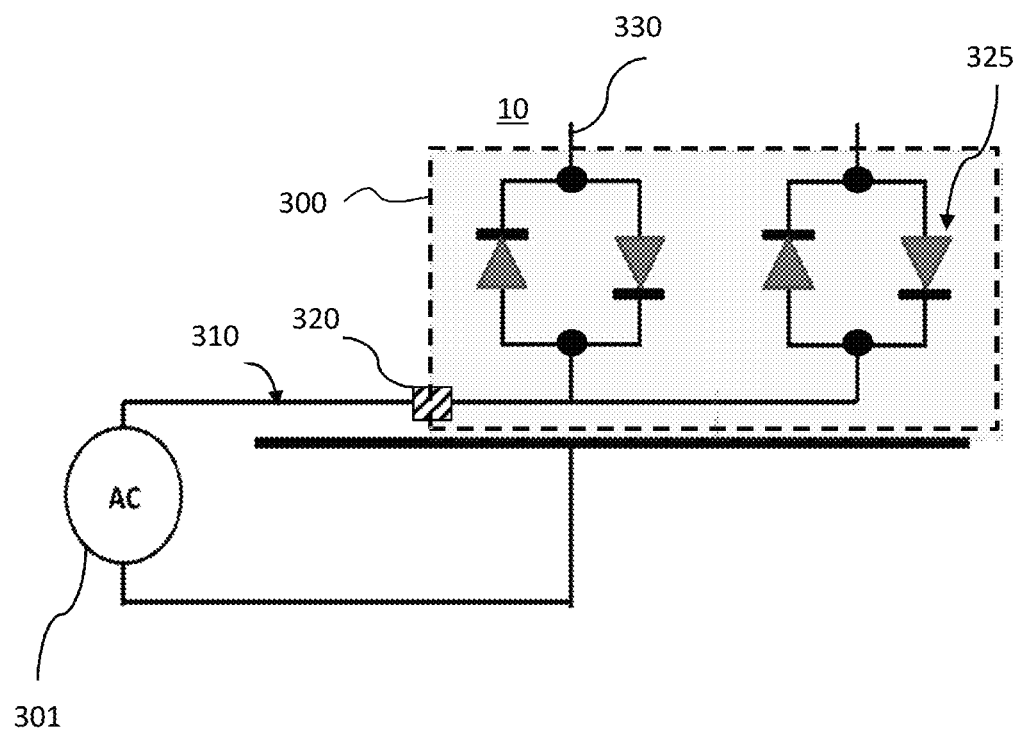
FIG. 3 shows a third example of a load arrangement having a galvanic front electrode.

FIG. 3 shows a third example of a load arrangement having a galvanic front electrode. In the example, the load is a set 325 of UV-C LEDs for emitting anti-fouling light coupled between first and second power nodes shown as black dots. The load arrangement comprises a carrier 300 as indicated by dashed lines and a conductor arrangement 310 shown as a conductor coupled to a back electrode 320. In a practical embodiment, the conductor arrangement may have metallic conductors arranged in a pattern distributed across the surface of the marine structure for coupling to a multitude of back electrodes of one or more carriers. The conductor arrangement may have a multi-lead cable configured to connect the leads to one pole of the power source and for separating and distributing the leads across the surface of the marine structure for coupling to a multitude of back electrodes. Alternatively, the conductor arrangement may have a wire-mesh structured for coupling to a multitude of back electrodes in a multitude of carriers and distributing the wire-mesh across the surface of the marine structure. The back electrodes may be arranged for coupling to the metallic conductors. In the example, the metallic conductors and at least one of the back electrodes are arranged for galvanic coupling.

The load arrangement may be similar to the example shown in FIG. 2, but has front electrodes 330 constituted by wire electrodes, e.g. made of Pt/Ti, that extend into the liquid 10. In this way, the galvanic front electrodes constitute a DC or low-frequency electrical connection via the sea water to a power source 301.

Optionally, powering the loads is combined with an ICCP corrosion prevention system, which may be present on the marine structure and may be independently powered using DC current from the power source 301 or a separate ICCP power source. To avoid overcurrent situations and electro-chemistry, the load arrangement may be operated using AC at a relatively high frequency, whereas the ICCP related part is operated DC or at rectified AC. Thus, independent control over load arrangement and ICCP is possible while still using the same wired infra-structure, which reduces cost. The high frequency chosen for the powering of the LED's avoids that electro-chemistry occurs by AC currents to the LEDs. On the other hand, the ICCP system only requires low currents, which may flow via the LEDs. So, the ICCP currents are not significantly affecting the UVC LED output for anti-fouling. Beneficially, the ICCP structure is now provided with a distributed set of anodes constituted by the transmitters 330 extending into the seawater, which improves reliability of the corrosion protection. Also, rather than a few discrete transmitter anodes conducting highly concentrated ICCP currents, said multiple anodes conducting low ICCP currents are distributed across the hull, thereby reducing electro and magnetic signatures of a vessel.

For electric safety and continued operation when damaged, the common supply wiring in the conductor arrangement may be made redundant, well-isolated and fused. In the case of supply wire damage, one or more not current-limited short-circuits may arise towards the seawater and, hence, to the CP, rudder and/or propeller (shaft) or directly to the hull. Redundant and/or fused supply lines may then be disabled, e.g. disconnected from the supply lines of the conductor arrangement. For example, carriers having multiple loads may also have multiple connections via back electrodes to different parts of the conductor arrangement. When some of such parts are disabled, power may still be provided via other parts of the conductor arrangement or via one or more loop-through connections to other carriers. Loop-through may provide a method for maintaining the electrical connection to most of the tiles while some connections inside or towards other tiles are broken. Similar redundancy occurs if parts of a mesh wire in the supporting layer are broken. However, a damage might also lead to a direct electrical connection between a main power lead and the seawater or the hull. For this situation, a current limiting or fusing approach is proposed.

In an embodiment of the load arrangement, the carrier comprises an inductor connected in series with the load for constituting, in combination with at least one of the back and front capacitors, a circuit resonant at a resonance frequency for cooperating with the power source generating an AC supply voltage at the resonance frequency. Effectively, by forming a resonant circuit, the impedance of the circuit as present between the conductors of the conductor arrangement and the liquid is lowered. Optionally, the carrier comprises a capacitor connected in series with the load. Such capacitance may further contribute to achieving a desired resonance frequency. Dimensioning the inductors and capacitors may be based on the following analysis.

The capacity of an AC capacitive plate transmitter is given by $$C=\varepsilon_0\varepsilon_r A/d$$

with A is the surface, d is the thickness of the gap from the plate to the sea water, $\varepsilon_0=8.854 \cdot 10^{-12}$ F/m, $\varepsilon_r=2.75$ (for silicone as material of the carrier). For a gap between 0.1 mm, and a plate surface of 50×50 mm², the value of the coupling capacitor is $C=6 \cdot 10^{-10}$ F. For a frequency of $f=100$ kHz the ac resistance is given by $$Z=1/i\omega C$$

So a typical value for $|Z|$ for this capacitor is $|Z|=2.6$ kOhm. This is larger than the typical resistance of an UVC LED which is about 6V/15 mA=400 Ohm. Hence if a single set of LED's is used, this leads to considerable power loss due to the resistance of the capacitive coupler. At higher frequency (e.g.>2 MHz) the resistance of the coupler is smaller and therefore the power loss is reduced.

The power loss may be prevented by placing an inductive coil L in series with the coupling capacitor. The total resistance of the capacitor and the inductor is given by $$Z=i\omega L+1/i\omega C$$

and $$|Z|=(1-\omega^2 LC)/\omega C$$

The value of $|Z|$ reduces to zero at the resonance frequency of $$\omega_r=1/\sqrt{LC}$$

At this resonance frequency, the capacitor loss is compensated for by the inductor. For $C=6 \cdot 10^{-10}$ F and $\omega_r=2\pi \cdot 1 \cdot 10^5=6 \cdot 10^5$ Hz, the required value of inductance is given by L=5 mH.

In an embodiment, the resonance frequency may be made different for different sections of the ship by choosing dedicated values for C and L. These sections can then be selectively powered by respective different AC power sources, or a controllable AC power source by tuning/adjusting the frequency to match with their specific resonance frequency.

It will be clear to a person skilled in the art that the invention is not limited to the examples discussed in the foregoing, but that several amendments and modifications thereof are possible. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species". Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

Finally, use of the above load arrangement is foreseen, in particular use of the load arrangement installed to an exposed surface of a marine structure for anti-fouling of the exposed surface when immersed in a fouling liquid containing biofouling organisms. The use requires the lighting arrangement to be powered by an AC power source having a sufficiently high frequency to pass the required power to the light source via the capacitor. So, the load arrangement according to the invention may be applied on a vessel's hull. Other examples of the exposed surface include the exterior surface of box coolers, surfaces of subsea off-shore equipment, interior walls of water reservoirs like ballast tanks of vessels, and filter surfaces of filter systems in desalination plants.

Summarizing, a load arrangement is provided for powering a load on a surface of a marine structure exposed to a liquid. The load arrangement has a carrier and a conductor arrangement arranged on the surface of the marine structure and coupled to one pole of a power source. The other pole is coupled to the liquid. The carrier has a back surface to cover part of the conductor arrangement and the surface of the marine structure. A load in the carrier receives supply current from the power source via a front electrode arranged for coupling to the liquid, and a back electrode at the back surface arranged for coupling to the conductor arrangement.

The invention claimed is:

1. A load arrangement comprising:
   a conductor arrangement, and
   wherein the conductor arrangement is arranged on a surface of a marine structure,
   wherein the conductor arrangement is arranged to couple to one pole of a power source,
   wherein, the other pole of the power source is coupled to an electrically conductive medium,
   wherein the electrically conductive medium is a liquid;
   a carrier, wherein the carrier has a front surface and a back surface, the carrier comprising a load arranged in the carrier,
       wherein the load is coupled between a first power node and a second power node,
       wherein the load is arranged to receive supply current from the power source,
   a front electrode at the front surface,
       wherein the front electrode is connected to the first power node,
       wherein the front electrode is arranged to couple to the electrically conductive medium; and
   a back electrode at the back surface,
       wherein the back electrode is connected to the second power node; and
       wherein the back electrode is arranged to couple to the conductor arrangement,
   wherein the front surface is arranged in contact with the liquid,
   wherein the back surface is arranged to cover at least a portion of the conductor arrangement; and
   wherein the back surface is arranged to cover at least a portion of the surface of the marine structure.

2. The load arrangement according to claim 1,
   wherein the front electrode comprises a conductive part at the front surface; and
   wherein the front electrode is galvanically in contact with the liquid for transfer of the supply current between the first power node and the electrically conductive medium.

3. The load arrangement according to claim 1,
   wherein the front electrode comprises a front electrically conductive layer,
   wherein the front electrode is embedded in the carrier near the front surface; and
   wherein the front electrically conductive layer is arranged to form, in combination with a dielectric layer and the liquid, a front capacitor for capacitive transfer of the supply current between the first power node and the electrically conductive medium.

4. The load arrangement according to claim 3,
   wherein the conductor arrangement comprises metallic conductors,
   wherein the conductor arrangement is arranged in a pattern distributed across the surface of the marine structure,
   wherein the conductor arrangement is arranged to couple to a multitude of back electrodes of one or more carriers; and
   wherein the back electrode is arranged to couple to the metallic conductors.

5. The load arrangement according to claim 4,
   wherein the metallic conductors are arranged for galvanic coupling; and
   wherein at least one of the back electrodes are arranged for galvanic coupling.

6. The load arrangement according to claim 5,
   wherein at least one of the back electrodes comprises a back electrically conductive layer embedded in the carrier near the back surface; and
   wherein at least one of the back electrodes is arranged to form, in combination with a back dielectric layer and an opposite area of the metallic conductors, a back capacitor for capacitive transfer of the supply current between the second power node and the metallic conductors.

7. The load arrangement according to claim 6,
wherein the carrier comprises an inductor connected in series with the load, in combination with at least one of the back capacitors and the front capacitors, a resonant circuit,
wherein the circuit resonant at a resonance frequency,
wherein the resonance frequency is arranged to cooperate with the power source; and
wherein the power source generates an AC supply voltage at the resonance frequency.

8. The load arrangement according to claim 1,
wherein the conductor arrangement comprises a multi-lead cable,
wherein the multi-lead cable is arranged to connect the leads to one pole of the power source; and
wherein the multi-lead cable is arranged to separate and distribute the leads across the surface of the marine structure for coupling to a multitude of back electrodes.

9. The load arrangement according to claim 1,
wherein the conductor arrangement comprises a wire-mesh; and
wherein the conductor arrangement is structured to couple to a multitude of back electrodes in a multitude of carriers and to distribute the wire-mesh across the surface of the marine structure.

10. The load arrangement according to claim 1,
wherein the carrier is shaped as a tile,
wherein the carrier comprises multiple of the loads,
wherein the carrier has interconnected second power nodes,
wherein the load arrangement comprises connector elements corresponding to edges of the tile,
wherein the edges of the tile are arranged to interconnect with neighboring tiles.

11. The load arrangement according to claim 1, wherein the carrier comprises a capacitor connected in series with the load.

12. The load arrangement according to claim 1,
wherein the carrier comprises an optical medium and the load comprises an UV light source,
wherein the UV light source is arranged to emit anti-fouling light,
wherein the anti-fouling light is arranged for anti-fouling of the carrier or a surface of the marine structure in contact with the liquid; and
wherein the liquid is a fouling liquid containing biofouling organisms.

13. A marine structure comprising:
a power source; and
a load arrangement, the load arrangement comprising:
a conductor arrangement,
wherein the conductor arrangement is arranged to couple to one pole of the power source,
wherein the other pole of the power source is coupled to an electrically conductive medium,
wherein the electrically conductive medium is a liquid; and
a carrier, wherein the carrier has a front surface and a back surface, the carrier comprising: a load arranged in the carrier,
wherein the load is coupled between a first power node and a second power node; and
wherein the load is arranged to receive supply current from the power source,
a front electrode at the front surface,
wherein the front electrode is connected to the first power node,
wherein the front electrode is arranged to couple to the electrically conductive medium; and
a back electrode at the back surface,
wherein the back electrode is connected to the second power node; and
wherein the back electrode is arranged to couple to the conductor arrangement,
wherein the front surface is arranged in contact with the liquid,
wherein the back surface is arranged to cover at least a portion of the conductor arrangement; and
wherein the back surface is arranged to cover at least a portion of the surface of the marine structure,
wherein the marine structure has a surface to be exposed to the liquid,
wherein the conductor arrangement is arranged on a first surface of the marine structure;
wherein the carrier is arranged at the first surface of the marine structure; and
wherein the back surface covers a portion of the conductor arrangement and the first surface of the marine structure.

14. The marine structure according to claim 13,
wherein the front electrode comprises a conductive part at the front surface galvanically in contact with the liquid,
wherein the front electrode is arranged to transfer supply current between the first power node and the electrically conductive medium,
wherein the back electrode is arranged for galvanic coupling to the conductor arrangement and for galvanically connecting the back electrode to the power source; and
wherein the power source is arranged to yield impressed current cathodic protection of the marine structure by adding a DC offset with respect to the marine structure to the supply voltage.

* * * * *